US012637406B2

(12) United States Patent
Yu et al.

(10) Patent No.: US 12,637,406 B2
(45) Date of Patent: May 26, 2026

(54) DIESTER STRUCTURE MONOMER, PREPARATION METHOD THEREFOR, AND APPLICATION THEREOF

(71) Applicant: NINGBO NATA OPTO-ELECTRONIC MATERIAL CO., LTD., Ningbo (CN)

(72) Inventors: Shaoshan Yu, Ningbo (CN); Dagong Gu, Ningbo (CN); Dongsheng Xu, Ningbo (CN); Tao Fang, Ningbo (CN); Guoqiang Qi, Ningbo (CN); Xiao Ma, Ningbo (CN); Zhibiao Mao, Ningbo (CN); Chongying Xu, Ningbo (CN)

(73) Assignee: NINGBO NATA OPTO-ELECTRONIC MATERIAL CO., LTD., Ningbo (CN)

( * ) Notice: Subject to any disclaimer, the term of this patent is extended or adjusted under 35 U.S.C. 154(b) by 1080 days.

(21) Appl. No.: 17/718,331

(22) Filed: Apr. 12, 2022

(65) Prior Publication Data

US 2022/0234985 A1 Jul. 28, 2022

Related U.S. Application Data

(63) Continuation of application No. PCT/CN2020/133731, filed on Dec. 4, 2020.

(30) Foreign Application Priority Data

Oct. 21, 2020 (CN) ......................... 202011129934.7

(51) Int. Cl.

| | |
|---|---|
| ***C07C 67/08*** | (2006.01) |
| ***C08J 5/18*** | (2006.01) |
| ***C08L 33/04*** | (2006.01) |

(52) U.S. Cl.

CPC ................. *C07C 67/08* (2013.01); *C08J 5/18* (2013.01); *C08L 33/04* (2013.01); *C08J 2333/04* (2013.01)

(58) Field of Classification Search

CPC ... C07C 67/08; C07C 2601/08; C07C 69/675; C07C 67/31; C07C 67/14; C08J 5/18;

(Continued)

(56) References Cited

U.S. PATENT DOCUMENTS

| | | | | |
|---|---|---|---|---|
| 5,891,935 A * | 4/1999 | Schneider | ............ | C09D 5/1668 526/240 |
| 2004/0063024 A1* | 4/2004 | Khojasteh | ............ | G03F 7/0395 430/326 |

(Continued)

FOREIGN PATENT DOCUMENTS

| | | |
|---|---|---|
| CN | 1398362 A | 2/2003 |
| CN | 1685285 A | 10/2005 |

(Continued)

OTHER PUBLICATIONS

Erol et al (Reactive and functional polymers (2003), 56 (3), 147-157.*

(Continued)

*Primary Examiner* — Jafar F Parsa

(74) *Attorney, Agent, or Firm* — Bayramoglu Law Offices LLC

(57) ABSTRACT

The preparation method for the diester structure monomer includes the following steps: dissolving glycolate in a reaction solvent to prepare a glycolate solution; mixing the glycolate solution with triethylamine in a protective atmosphere, and cooling to form a mixture; and keeping the protective atmosphere unchanged, and adding the methacryloyl chloride to the mixture for esterification to generate a diester structure monomer. The diester structure monomer (Continued)

generated by the preparation method for the diester structure monomer has a long diester side chain and a group with a small volume and high acid sensitivity. As a result, a resin synthesized from the diester structure monomer has good adhesive force and film-forming property, high deprotection efficiency and plasticity, and the hardness and brittleness of the resin are improved. Moreover, the prepared diester acid protected structure monomer has the advantages of high yield, low by-product content and easy separation and purification.

10 Claims, 2 Drawing Sheets

(58) Field of Classification Search
CPC .. C08J 33/04; C08J 2333/04; C08F 220/1805; C08F 2200/1808; C08F 220/283
See application file for complete search history.

(56) References Cited

U.S. PATENT DOCUMENTS

| | | | | |
|---|---|---|---|---|
| 2009/0326095 | A1* | 12/2009 | Badejo | A61L 15/58 523/118 |
| 2012/0283378 | A1* | 11/2012 | Shoshi | C07F 7/0838 524/556 |
| 2013/0130178 | A1* | 5/2013 | Iizuka | C08F 12/22 430/281.1 |
| 2016/0284559 | A1 | 9/2016 | Kikuchi et al. | |
| 2018/0118887 | A1* | 5/2018 | Shibuya | C08G 73/1042 |

FOREIGN PATENT DOCUMENTS

| | | | | |
|---|---|---|---|---|
| CN | 1690851 | A | 11/2005 | |
| CN | 106963733 | A | 7/2017 | |
| CN | 107596383 | A | 1/2018 | |
| CN | 108693703 | A | 10/2018 | |
| CN | 110590554 | A | 12/2019 | |
| JP | 2010256873 | A | 11/2010 | |
| JP | 2011186244 | A | 9/2011 | |
| JP | 2012013961 | * | 1/2012 | C08J 2333/04 |
| JP | 2012013961 | A | 1/2012 | |
| JP | 2013120245 | * | 6/2013 | C08J 2333/04 |
| TW | 201219424 | A | 5/2012 | |

OTHER PUBLICATIONS

Changri Han, et al., Production process and technology of chemicals used in electronics and information, 2019, pp. 347, Science and Technology Literature Publishing House.

* cited by examiner

DIESTER STRUCTURE MONOMER, PREPARATION METHOD THEREFOR, AND APPLICATION THEREOF

CROSS REFERENCE TO THE RELATED APPLICATIONS

This application is a continuation application of International Application No. PCT/CN2020/133731, filed on Dec. 4, 2020, which is based upon and claims priority to Chinese Patent Application No. 202011129934.7, filed on Oct. 21, 2020, the entire contents of which are incorporated herein by reference.

TECHNICAL FIELD

The present invention belongs to the technical field of photoresists, and particularly relates to a diester structure monomer, a preparation method therefor, and an application thereof.

BACKGROUND

As a photosensitive high molecular material with high sensitivity to light and rays, photoresists are mainly used in such fields as micrograph processing for integrated circuits and discrete semiconductor devices, and production of panel displays in the field of optoelectronics. As electronic devices are developing towards high integration and high speed, photoresists are becoming increasingly important. A photoresist is generally made up of a film-forming resin, a photosensitizer, a solvent, and additives, where the film-forming resin is one of the important components of the photoresist and plays a decisive role in performance of the photoresist.

Existing film-forming resins are mainly divided into three categories: 1. poly(meth)acrylates; 2. cycloolefin-maleic anhydride copolymers; and 3. norbornene polymers, where poly(meth)acrylates are the most widely used, but due to deficiencies of monomer structures of poly(meth)acrylates, photoresists prepared therefrom have various defects, and these defects ultimately affect performance of photolithography products, such as low purity of monomers, high hardness and brittlement of films due to rigid structures of the monomers, poor adhesive force and film-forming property because molecular weights of the monomers affect viscosity of the photoresists, and poor corrosion resistance of the photoresists due to defects of acid sensitive groups of the monomers. These defects can only be resolved by constantly improving monomer structures of the film-forming resins.

SUMMARY

An objective of the present invention is to overcome the deficiencies in the prior art and provide a diester structure monomer and a preparation method therefor to resolve the technical problems of poor adhesive force and film-forming property and poor corrosion resistance of existing film-forming resins due to deficiencies of monomer structures of the film-forming resins.

Another objective of the present invention is to provide a film-forming resin and a photoresist containing the film-forming resin to resolve the technical problems of poor adhesive force and film-forming property and poor corrosion resistance of photoresists due to unsatisfactory performance of existing film-forming resins.

To achieve the objectives, a first aspect of the present invention provides a preparation method for a diester structure monomer. The preparation method for the diester structure monomer includes the following steps:

dissolving glycolate in a reaction solvent to prepare a glycolate solution;

mixing the glycolate solution with triethylamine in a protective atmosphere, and cooling to form a mixture; and keeping the protective atmosphere unchanged, and adding the methacryloyl chloride to the mixture for esterification to generate a diester structure monomer with the following general molecular structural formula I:

(I)

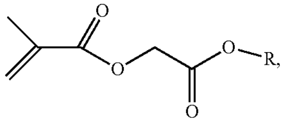

where R in the general formula I is any one of methyl, ethyl, propyl, butyl, amyl, aryl, phenyl,

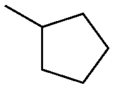,
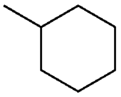,
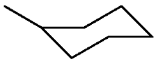, adamantyl and alkyl with a polycyclic structure.

Another aspect of the present invention provides a diester structure monomer. The diester structure monomer has a general molecular structural formula I as follows:

(I)

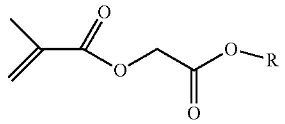

where R in the general formula I is any one of methyl, ethyl, propyl, butyl, amyl, aryl, phenyl,

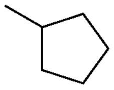,
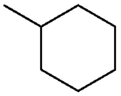,
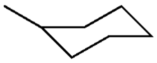, adamantyl and alkyl with a polycyclic structure.

Another aspect of the present invention provides a film-forming resin. The film-forming resin includes the diester structure monomer prepared by the preparation method of the present invention or the diester structure monomer as described herein.

Another aspect of the present invention provides a photoresist. The photoresist includes the film-forming resin of the present invention.

Compared with the prior art, according to the preparation method for the diester structure monomer of the present invention, esterification is carried out by selecting reactants to generate a diester structure monomer, and the diester structure monomer is endowed with a long diester side chain and a group with a small volume and high acid sensitivity; the long diester side chain group endows a resin synthesized from the diester structure monomer with good adhesive force and film-forming property; and the group with a small volume and high acid sensitivity endows a resin synthesized from the diester structure monomer with high deprotection efficiency and plasticity, and hardness and brittleness of the resin are improved. Moreover, by adjusting a technological process and parameters, the diester acid protected structure monomer prepared by the preparation method has the advantages of high yield, low by-product content and easy separation and purification.

The diester structure monomer of the present invention has a long diester side chain and a group with a small volume and high acid sensitivity; the long diester side chain group endows a resin synthesized from the diester structure monomer with good adhesive force and film-forming property; and the group with a small volume and high acid sensitivity endows a resin synthesized from the diester structure monomer with high deprotection efficiency and plasticity, and hardness and brittleness of the resin are improved.

The film-forming resin of the present invention includes the diester structure monomer of the present invention, so that the film-forming resin has good adhesive force and film-forming property, high deprotection efficiency and plasticity, and hardness and brittleness of the film-forming resin are more suited to application requirements of photoresists.

Because the photoresist of the present invention contains the film-forming resin of the present invention, the photoresist has good adhesive force and film-forming property, high deprotection efficiency and high plasticity, so that photolithography effect is improved.

BRIEF DESCRIPTION OF THE DRAWINGS

In order to explain the technical solutions in specific implementations of the present invention or in the prior art more clearly, the drawings used in the description of the specific implementations or the prior art will be briefly introduced below. Obviously, the drawings in the following description are some implementations of the present invention. For those of ordinary skill in the art, other drawings can be obtained based on these drawings without creative effort.

DETAILED DESCRIPTION OF THE EMBODIMENTS

Figure 1:
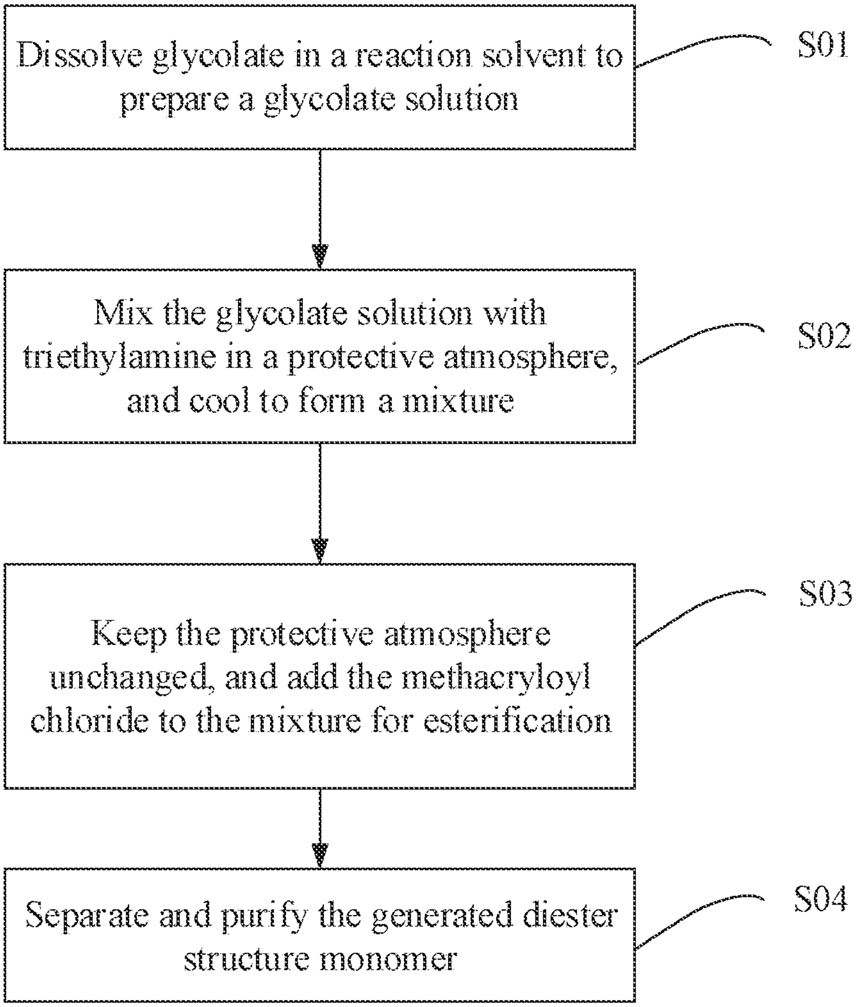
FIG. 1 is a schematic flow chart of a preparation method for a diester structure monomer according to an embodiment of the present invention.

To make the technical problems to be resolved, technical solutions and beneficial effects of the present invention clearer, the present invention will be further described in detail with reference to the embodiments. It should be understood that specific embodiments described herein are merely intended to explain the present invention, but not intended to limit the present invention. Based on the embodiments of the present invention, all other embodiments obtained by those of ordinary skill in the art without creative efforts should fall within the protection scope of the present invention.

The term "and/or" in this application describes an association relationship between associated objects and represents that three relationships may exist. For example, "A and/or B" may represent the following three cases: Only A exists, both A and B exist, and only B exists. A and B may be singular or plural. The character "/" generally indicates an "or" relationship between associated objects.

In this application, "at least one" means one or more, and "a plurality of" means two or more than two. "At least one of the following" or similar expression refers to any combination of these items, including an item or any combination of items. For example, "at least one of a, b, or C" or "at least one of a, b, and C" may mean: a, b, c, a-b (that is, a and b), a-c, b-c, or a-b-c, where a, b, and c may be singular or plural.

As used herein, the terms "comprising", "including", "having", "containing" or any other variation thereof are intended to cover a non-exclusive inclusion. For example, a composition, step, method, article or apparatus that includes a list of elements is not necessarily limited to only those elements, but may include other elements not explicitly listed or inherent to such composition, step, method, article or apparatus.

When equivalents, concentrations, or other values or parameters are expressed as ranges, preferred ranges, or ranges defined by a series of preferred upper limit values and preferred lower limit values, it should be understood as specifically disclosing all ranges formed by any pairing of any range upper limit or preferred value with any range lower limit or preferred value, regardless of whether the ranges are individually disclosed. For example, when a range "1 to 5" is disclosed, the described range should be interpreted as including ranges "1 to 4", "1 to 3", "1 to 2", "1 to 2 and 4 to 5", "1 to 3 and 5", and the like. When a numerical range is described herein, unless otherwise indicated, the range is intended to include its end values and all integers and fractions within the range.

In addition, the indefinite articles "a" and "an" before an element or component in the present invention do not limit the quantity requirements (i.e., the number of occurrences) of the element or component. Therefore, "a" or "an" should be interpreted as including one or at least one, and an element or component in the singular form also includes the plural form thereof, unless the number clearly refers to the singular form.

In various embodiments of this application, sequence numbers of the foregoing processes do not mean execution sequences, and some or all steps may be executed in parallel or successively. The execution sequences of the processes should be determined according to functions and internal logic of the processes, and should not be construed as any limitation to the implementation processes of the embodiments of this application.

Weights of relevant components mentioned in the specification of the embodiments of this application may refer to contents of the components, and indicate a proportional relationship between weights of the components. Therefore, contents of relevant components scaled up or down according to the specification of the embodiments of this application are within the scope disclosed in the specification of the embodiments of this application. Specifically, masses in the specification of the embodiments of this application may be μg, mg, g, kg, and other units of mass known in the chemical industry.

According to an aspect, an embodiment of the present invention provides a diester structure monomer compound. The diester structure monomer has a general molecular structural formula I as follows:

(I)

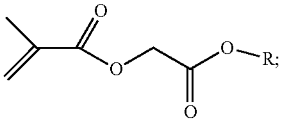

where the R group in the general formula I may be any one of methyl (Me), ethyl (Et), propyl (Pr), butyl (Bu), amyl (Am), aryl (Ar), phenyl (Ph),

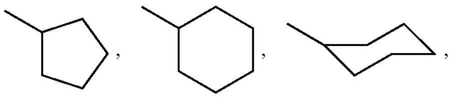

adamantyl and alkyl with a polycyclic structure; where the propyl (Pr) preferably isopropyl (iPr), the butyl (Bu) is preferably tert-butyl (tBu), and the amyl (Am) is preferably isoamyl (iAm).

According to the general molecular structural formula I, the diester structure monomer has a long diester side chain and a group with a small volume and high acid sensitivity. The long diester side chain group endows a resin synthesized from the diester structure monomer with good adhesive force and film-forming property; and the group with a small volume and high acid sensitivity endows a resin synthesized from the diester structure monomer with high deprotection efficiency and plasticity, and hardness and brittleness of the resin are improved.

According to another aspect, an embodiment of the present invention provides a preparation method for the diester structure monomer. A process flow of the preparation method for the diester structure monomer is shown in FIG. 1, including the following steps:

S01: dissolving glycolate in a reaction solvent to prepare a glycolate solution;

S02: mixing the glycolate solution with triethylamine in a protective atmosphere, and cooling to form a mixture; and

S03: keeping the protective atmosphere unchanged, and adding the methacryloyl chloride to the mixture for esterification to generate a diester structure monomer with the following general molecular structural formula I:

(I)

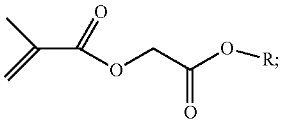

where R in the general formula I is any one of methyl, ethyl, propyl, butyl, amyl, aryl, phenyl,

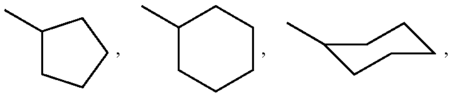

adamantyl and alkyl with a polycyclic structure.

According to the preparation method for the diester structure monomer, esterification is carried out by selecting reactants to generate a diester structure monomer, and the diester structure monomer is endowed with a long diester side chain and a group with a small volume and high acid sensitivity; the long diester side chain group endows a resin synthesized from the diester structure monomer with good adhesive force and film-forming performance; and the group with a small volume and high acid sensitivity endows a resin synthesized from the diester structure monomer with high deprotection efficiency and plasticity, and hardness and brittleness of the resin are improved.

In the step S01, stability of the glycolate should be ensured when the glycolate is dissolved in the reaction solvent. For example, in one embodiment, the glycolate is dissolved in the reaction solvent in a protective atmosphere. In another embodiment, the glycolate is dissolved in the reaction solvent at a molar ratio of the glycolate to the reaction solvent of 1:(5-10) to ensure complete dissolution of the glycolate to form a homogeneous solution, and control concentration of an esterification system in the step S03, so as to improve yield of a target product and increase a reaction rate.

In a specific embodiment, the reaction solvent is selected from one or more of dichloromethane, tetrahydrofuran, trichloromethane, diethyl ether, toluene and dichloroethane. By selecting a reaction solvent, solubility of the glycolate is improved, and a reaction system favorable for the generation of a target product is constructed for the esterification in the step S03, so as to improve yield of the target product and reduce the generation of by-products.

In another specific embodiment, the glycolate reactant may be a glycolate compound containing an R group in the following chemical reaction formula (1). The R group may be any one of methyl (Me), ethyl (Et), propyl (Pr), butyl (Bu), amyl (Am), aryl (Ar), phenyl (Ph),

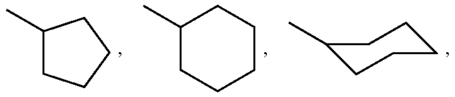

adamantyl and alkyl with a polycyclic structure; where the propyl (Pr) is preferably isopropyl (iPr), the butyl (Bu) is preferably tert-butyl (tBu), and the amyl (Am) is preferably isoamyl (iAm).

The glycolate solution should be fully mixed with triethylamine in the step S02, and the more uniform the mixing, the better. In one embodiment, the glycolate solution is mixed with triethylamine at a molar ratio of the glycolate to the triethylamine of 1:(1-1.3). A ratio of reactants in the esterification system in the step S03 is optimized by mixing the glycolate solution with triethylamine at a ratio to improve yield of a target product.

In one embodiment, the cooling in the step S02 is carried out by using ice water to reduce temperature of a mixture system, so as to facilitate the esterification in the step S03.

In the step S03, methacryloyl chloride is added to the mixture for the esterification based on the following chemical reaction formula:

(1)

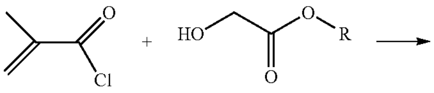

-continued

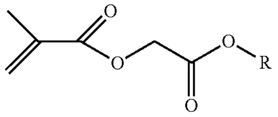

In one embodiment, the methacryloyl chloride is added to the mixture at a molar ratio of the glycolate to the methacryloyl chloride of 1:(1-1.1). A ratio of reactants in the esterification system in the step S03 is optimized by controlling a mixing ratio of the reactants to improve yield of a target product.

In another embodiment, the methacryloyl chloride is added dropwise to the mixture at a speed of 0.01-0.05 ml/s. The rate of adding the methacryloyl chloride is controlled to improve yield of a target product and reduce the generation of by-products.

In another embodiment, the esterification is controlled to be carried out at 20-35° C. for 4-8 h. The esterification temperature and time are controlled to increase an esterification rate, improve yield of a target product and reduce the generation of by-products.

In a further embodiment, the preparation method further includes a step S04 of separating and purifying the generated diester structure monomer as shown in FIG. 1 after the esterification step. The step of separating and purifying the generated diester structure monomer includes:

carrying out filtration, washing, separation and distillation sequentially on a reaction mixture subjected to the esterification to obtain a purified diester structure monomer.

The filtration may be carried out by a conventional filtering method to collect a filtrate. The filtrate may be washed directly with water to remove impurities such as solvent. The separation is preferably carried out by the following method: filtering the reaction mixture under vacuum to remove solid particles, then washing a filtrate with water for several times, separating an organic phase, adding anhydrous magnesium sulfate for drying, then filtering the organic phase, concentrating a filtrate under vacuum, and finally distilling the filtrate under vacuum.

In one embodiment, a polymerization inhibitor is added to the reaction mixture in the distillation step to avoid subsequent polymerization of the target product in the distillation. In one embodiment, the polymerization inhibitor is added to the reaction mixture at a molar ratio of the glycolate to the polymerization inhibitor of 1:(0.01-0.1). In a specific embodiment, the polymerization inhibitor is at least one of 2,2,6,6-tetramethyl-4-hydroxypiperidine nitroxyl radical, N—N-copper di-n-butyldithiocarbamate, phenothiazine and p-hydroxyanisole.

Therefore, the diester structure monomer generated by the preparation method for the diester structure monomer in the embodiment of the present invention has a long diester side chain and a group with a small volume and high acid sensitivity; so that a resin synthesized from the diester structure monomer has good adhesive force and film-forming property, high deprotection efficiency and plasticity, and hardness and brittleness of the resin are improved. Moreover, by adjusting a technological process and parameters, the diester acid protected structure monomer prepared by the preparation method has the advantages of high yield, low by-product content and easy separation and purification.

According to another aspect, an embodiment of the present invention further provides a film-forming resin and a photoresist containing the film-forming resin based on the diester structure monomer and the preparation method therefor described above.

A monomer of the film-forming resin is the diester structure monomer in the embodiment of the present invention, that is, the diester structure monomer as shown in the general molecular structural formula I, specifically 2-tert-butoxy-2-oxoethyl methacrylate. In a specific embodiment, the film-forming resin is a polymer generated by polymerization of the diester structure monomer as shown in the general molecular structural formula I. The film-forming resin includes the diester structure monomer of the present invention, so that the film-forming resin has good adhesive force and film-forming property, high deprotection efficiency and plasticity, and hardness and brittleness of the film-forming resin are more suited to application requirements of photoresists.

The photoresist contains necessary components of photoresists, such as a film-forming resin and other components, the film-forming resin is the film-forming resin in the embodiment of the present invention, and is also a film-forming resin containing the diester structure monomer as shown in the general molecular structural formula I. Because the photoresist contains the diester structure monomer in the embodiment of the present invention, the photoresist has good adhesive force and film-forming property, high deprotection efficiency and high plasticity, so that photolithography effect is improved.

The preparation method for the diester structure monomer in the embodiments of the present invention is illustrated in combination with specific embodiments.

1. Embodiments of Diester Structure Monomer and Preparation Method Therefor

Embodiment 1

This embodiment provides a diester structure monomer of 2-methoxy-2-oxoethyl methacrylate and a preparation method therefor. The preparation method for 2-methoxy-2-oxoethyl methacrylate includes the following steps:

S1: adding 0.90 g of methyl glycolate to a Schlenk flask, and fully replacing a system in the flask by N2 to fill the flask with a N2 atmosphere;

S2: adding 75 ml of dichloromethane, a dehydrated organic solvent, to the Schlenk flask under the protection of N2, and stirring to completely dissolve methyl glycolate;

S3: adding 10.1 g of triethylamine to the Schlenk flask under the protection of N2, and cooling the Schlenk flask in an ice-water bath;

S4: adding 10.4 g of methacryloyl chloride dropwise to the Schlenk flask in the ice-water bath at a speed of 0.05 ml/s under the protection of N2, and stirring constantly;

S5: after adding the methacryloyl chloride dropwise, allowing a resulting mixture to react at 35° C. for 4 h under the protection of N2; and

S6: filtering the reaction solution, washing with 50 mL of purified water for three times, separating and concentrating an organic matter, and then adding 0.1 g of phenothiazine for vacuum distillation to obtain a colorless liquid, that is, a diester structure monomer of 2-methoxy-2-oxoethyl methacrylate. The yield is measured to be 92%.

Embodiment 2

This embodiment provides a diester structure monomer of 2-isopropoxy-2-oxoethyl methacrylate and a preparation method therefor. The preparation method for 2-isopropoxy-2-oxoethyl methacrylate includes the following steps:

S1: adding 11.8 g of isopropyl glycolate to a Schlenk flask, and fully replacing a system in the flask by N2 to fill the flask with a N2 atmosphere;

S2: adding 60 ml of dichloromethane, a dehydrated organic solvent, to the Schlenk flask under the protection of N2, and stirring to completely dissolve isopropyl glycolate;

S3: adding 11.2 g of triethylamine to the Schlenk flask under the protection of N2, and cooling the Schlenk flask in an ice-water bath;

S4: adding 11.6 g of methacryloyl chloride dropwise to the Schlenk flask in the ice-water bath at a speed of 0.05 ml/s under the protection of N2, and stirring constantly;

S5: after adding the methacryloyl chloride dropwise, allowing a resulting mixture to react at 25° C. for 6 h under the protection of N2; and S6: filtering the reaction solution, washing with 6 mL of purified water for three times, separating and concentrating an organic matter, and then adding 0.2 g of phenothiazine for vacuum distillation to obtain a colorless liquid, that is, a diester structure monomer of 2-isopropoxy-2-oxoethyl methacrylate. The yield is measured to be 90%.

Embodiment 3

This embodiment provides a diester structure monomer of 2-tert-butoxy-2-oxoethyl methacrylate and a preparation method therefor. The preparation method for 2-tert-butoxy-2-oxoethyl methacrylate includes the following steps:

S1: adding 13.2 g of tert-butyl glycolate to a Schlenk flask, and fully replacing a system in the flask by N2 to fill the flask with a N2 atmosphere;

S2: adding 80 ml of dichloromethane, a dehydrated organic solvent, to the Schlenk flask under the protection of N2, and stirring to completely dissolve tert-butyl glycolate;

S3: adding 11.1 g of triethylamine to the Schlenk flask under the protection of N2, and cooling the Schlenk flask in an ice-water bath;

S4: adding 13.2 g of methacryloyl chloride dropwise to the Schlenk flask in the ice-water bath at a speed of 0.03 ml/s under the protection of N2, and stirring constantly;

S5: after adding the methacryloyl chloride dropwise, allowing a resulting mixture to react at 30° C. for 5 h under the protection of N2; and S6: filtering the reaction solution, washing with 60 mL of purified water for three times, separating and concentrating an organic matter, and then adding 0.15 g of phenothiazine for vacuum distillation to obtain a colorless liquid, that is, a diester structure monomer of 2-tert-butoxy-2-oxoethyl methacrylate. The yield is measured to be 88%.

Embodiment 4

This embodiment provides a diester structure monomer of 2-cyclopentyloxy-2-oxoethyl methacrylate and a preparation method therefor. The preparation method for 2-cyclopentyloxy-2-oxoethyl methacrylate includes the following steps:

S1: adding 14.4 g of cyclopentylglycolate to a Schlenk flask, and fully replacing a system in the flask by N2 to fill the flask with a N2 atmosphere;

S2: adding 80 ml of dichloromethane, a dehydrated organic solvent, to the Schlenk flask under the protection of N2, and stirring to completely dissolve cyclopentylglycolate;

S3: adding 11.1 g of triethylamine to the Schlenk flask under the protection of N2, and cooling the Schlenk flask in an ice-water bath;

S4: adding 13.2 g of methacryloyl chloride dropwise to the Schlenk flask in the ice-water bath at a speed of 0.02 mils under the protection of N2, and stirring constantly;

S5: after adding the methacryloyl chloride dropwise, allowing a resulting mixture to react at 30° C. for 5 h under the protection of N2; and S6: filtering the reaction solution, washing with 60 mL of purified water for three times, separating and concentrating an organic matter, and then adding 0.15 g of phenothiazine for vacuum distillation to obtain a colorless liquid, that is, a diester structure monomer of 2-cyclopentyloxy-2-oxoethyl methacrylate. The yield is measured to be 85%.

Figure 2:
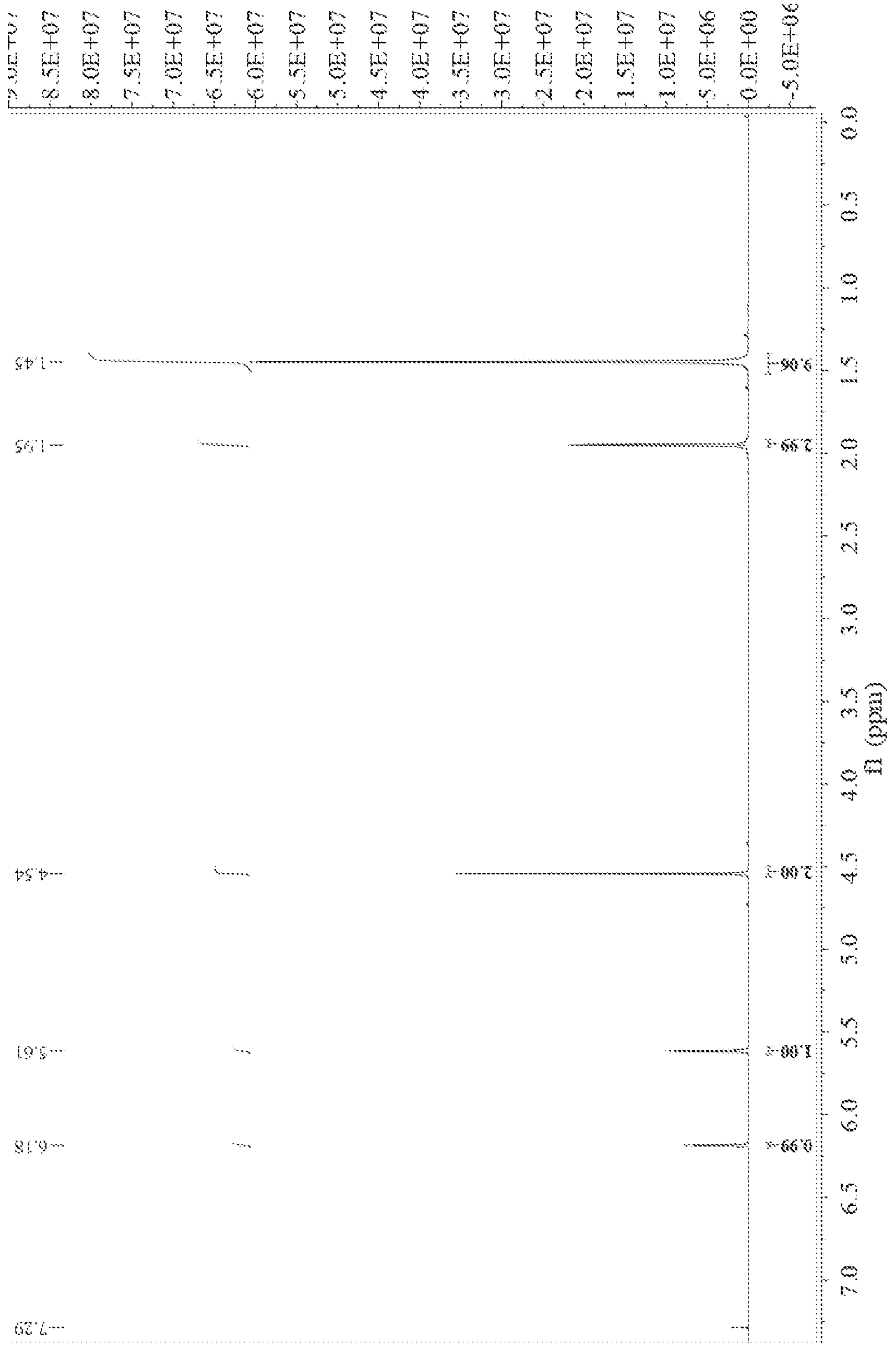
FIG. 2 is an NMR image of a diester structure monomer of 2-tert-butoxy-2-oxoethyl methacrylate according to Embodiment 3 of the present invention.

NMR spectroscopy is carried out on the diester structure monomer of 2-tert-butoxy-2-oxoethyl methacrylate provided in the embodiments, with an NMR image as shown in FIG. 2. According to FIG. 2, the diester structure monomer provided in the embodiments is 2-tert-butoxy-2-oxoethyl methacrylate.

2. Application Embodiments of Diester Structure Monomer

Embodiment 5

This embodiment provides a photoresist resin (or film-forming resin), and a preparation method for the photoresist resin (or film-forming resin) includes the following steps:

(1) adding 37 g of 1-ethylcyclohexyl methacrylate monomer, 48 g of cyclopentyl methacrylate, 25 g of 2-tert-butoxy-2-oxoethyl methacrylate and 50 g of tetrahydrofuran to a reactor filled with nitrogen, heating the reactor to 75° C. after stirring well, and then adding a mixture of 10 g of first tetrahydrofuran and 1.5 g of dibenzoyl peroxide dropwise to the reactor (for 30 min) for reaction at 75° C. for 24 h, then stopping the reaction and cooling the reactor to room temperature;

(2) adding 2000 g of first methanol to the reactor cooled to room temperature in the step (1), leading liquid out of the reactor 1 h after a precipitate is produced, and then adding second ethyl acetate to the reactor until the precipitate is dissolved; and (3) adding 2000 g of second methanol to the reactor in the step (2), repeating operations in the step (2) for three times to obtain a solid precipitate, and drying the solid precipitate under vacuum at 70° C. for 8 h to obtain 86 g ArF photoresist resin; and measuring molecular weight Mw=21246 and PDI=1.51 of the resin by a GPC.

Comparative Example 1

This comparative example provides a photoresist resin (or film-forming resin), and a preparation method for the photoresist resin (or film-forming resin) includes the following steps:

(1) adding 37 g of 1-ethylcyclohexyl methacrylate monomer, 48 g of cyclopentyl methacrylate and 50 g of tetrahydrofuran to a reactor filled with nitrogen, heating the reactor to 75° C. after stirring well, and then adding a mixture of 10 g of first tetrahydrofuran and 1.5 g of dibenzoyl peroxide dropwise to the reactor (for 30 min) for reaction at 75° C. for 24 h, then stopping the reaction and cooling the reactor to room temperature;

(2) adding 2000 g of first methanol to the reactor cooled to room temperature in the step (1), leading liquid out of the reactor 1 h after a precipitate is produced, and then adding second ethyl acetate to the reactor until the precipitate is dissolved; and (3) adding 2000 g of second methanol to the reactor in the step (2), repeating operations in the step (2) for three times to obtain a solid precipitate, and drying the solid precipitate under vacuum at 70° C. for 8 h to obtain 56 g ArF photoresist resin; and measuring molecular weight Mw=20146 and PDI=1.47 of the resin by a GPC.

3. Experiments for Evaluation of Film-Forming Property of Photoresists and Quality of Photolithography Products The ArF photoresist resin provided in Embodiment 5 is prepared into a photoresist based on the following formulation: 8.2 g of ArF photoresist resin provided in Embodiment 5, 0.12 g of triphenylsulfoniumnonaflate as a photosensitizer, 0.0091 g of N,N-dibutylaniline, 56 g of propylene glycol methyl ether acetate and 24 g of propylene glycol methyl ether; photolithography conditions: baking at 120° C. for 1.5 min, exposure energy: 10-50 mj/cm2, and developing time: 60 s. According to a final photolithography pattern, edges of independent lines of the photoresist are uniform without adhesion and collapse.

The ArF photoresist resin provided in Comparative Example 1 is prepared into a photoresist based on the following formulation: 8.2 g of ArF photoresist resin provided in Comparative Example 1, 0.12 g of triphenylsulfoniumnonaflate as a photosensitizer, 0.0091 g of N,N-dibutylaniline, 56 g of propylene glycol methyl ether acetate and 24 g of propylene glycol methyl ether photolithography conditions: baking at 120° C. for 1.5 min, exposure energy: 10-50 mj/cm2, and developing time: 60 s. According to a final photolithography pattern, edges of independent lines of the photoresist are non-uniform with adhesion and collapse.

According to the experiments for evaluation of film-forming property of photoresists and quality of photolithography products in this section, it can be known that the photoresist prepared from the diester acid protected structure monomer prepared by a specific process in the embodiments of the present invention has better toughness, film-forming property, corrosion resistance and the like, so that the photolithography product has better quality.

The foregoing descriptions are merely preferred embodiments of the present invention and are not intended to limit the present invention. Any modification, equivalent replacement and improvement made within the spirit and principle of the present invention shall be included in the protection scope of the present invention.

What is claimed is:

1. A diester structure monomer having a general molecular structural formula I as follows:

(I)

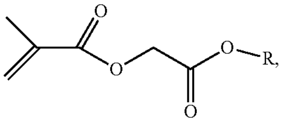

wherein R in the general molecular structural formula I is

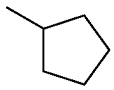, 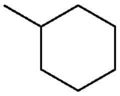, 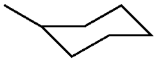,

2. A film-forming resin, comprising the diester structure monomer according to claim 1, the diester structure monomer being prepared by a process comprising the following steps:

(1) dissolving glycolate in a reaction solvent to prepare a glycolate solution;

(2) mixing the glycolate solution with triethylamine in a protective atmosphere, and cooling to form a mixture;

(3) keeping the protective atmosphere unchanged, and adding methacryloyl chloride to the mixture to obtain a reaction mixture; and (4) performing an esterification with the reaction mixture to generate the diester structure monomer.

3. A photoresist, comprising the film-forming resin according to claim 2.

4. The film-forming resin according to claim 2, wherein at least one of the following conditions are applied in the preparation method:

in step 1, a molar ratio of the glycolate to the reaction solvent is 1:(5-10);

in step 2, a molar ratio of the glycolate to the triethylamine is 1:(1-1.3); and in step 3, a molar ratio of the glycolate to the methacryloyl chloride is 1:(1-1.1).

5. The film-forming resin according to claim 2, wherein in step 3, the methacryloyl chloride is added dropwise to the mixture at a speed of 0.01-0.05 ml/s; and/or in step 4, the esterification is carried out at 20-35° C. for 4-8 h.

6. The film-forming resin according to claim 2, wherein in step 1, the reaction solvent is at least one solvent selected from the group consisting of dichloromethane, tetrahydrofuran, trichloromethane, diethyl ether, toluene, and dichloroethane; and/or the cooling is carried out by using ice water.

7. The film-forming resin according to claim 2, further comprising:

5) separating and purifying the diester structure monomer generated after the esterification, comprising: carrying out filtration, washing, separation, and distillation sequentially on the reaction mixture subjected to the esterification to obtain a purified diester structure monomer.

8. The film-forming resin according to claim 7, wherein in the distillation, a polymerization inhibitor is added to the reaction mixture.

9. The film-forming resin according to claim 8, wherein the polymerization inhibitor is added to the reaction mixture at a molar ratio of the glycolate to the polymerization inhibitor of 1:(0.01-0.1); and/or the polymerization inhibitor is at least one selected from the group consisting of 2,2,6,6-tetramethyl-4-hydroxypiperidine nitroxyl radical, N—N-copper di-n-butyldithiocarbamate, phenothiazine, and p-hydroxyanisole.

10. A film-forming resin, comprising the diester structure monomer according to claim 1.

* * * * *